United States Patent [19]

Foss

[11] 4,325,247
[45] Apr. 20, 1982

[54] METHOD FOR DETERMINING GASEOUS CONTAMINANTS IN VAPOR COOLED TRANSFORMERS

[75] Inventor: Stephen D. Foss, Pittsfield, Mass.
[73] Assignee: General Electric Company
[21] Appl. No.: 168,062
[22] Filed: Jul. 14, 1980
[51] Int. Cl.³ .............................................. G01N 7/14
[52] U.S. Cl. ..................................................... 73/19
[58] Field of Search ............. 73/19, 23, 37, 40, 863.81
[56] References Cited

U.S. PATENT DOCUMENTS

| | | | |
|---|---|---|---|
| 2,741,911 | 4/1956 | Fitzpatrick et al. | 73/19 |
| 4,101,277 | 7/1978 | Hickam | 73/23 |
| 4,236,404 | 12/1980 | Ketchum et al. | 73/19 |

FOREIGN PATENT DOCUMENTS 705303  12/1979  U.S.S.R. .................................. 73/19

*Primary Examiner*—Stephen A. Kreitman
*Attorney, Agent, or Firm*—Robert A. Cahill

[57] ABSTRACT

A pair of calibrated cylinders are connected by means of an interconnecting valve with an inlet valve at one end of one cylinder and a pressure gauge connected to one end of the other cylinder. The first cylinder is filled with condensable coolant containing a noncondensable gas contaminant and is valved off to the atmosphere. When the interconnecting valve between the cylinders is opened the condensable coolant and noncondensable gas are allowed to volatilize into the other cylinder until thermal equilibrium is established between both cylinders. The absolute pressure, which is equal to the sum of the partial pressure of the noncondensable gas and the known vapor pressure of the coolant at the equilibrium temperature, allows the quantity of noncondensable gas to be determined using Henry's Law.

5 Claims, 3 Drawing Figures

METHOD FOR DETERMINING GASEOUS CONTAMINANTS IN VAPOR COOLED TRANSFORMERS

BACKGROUND OF THE INVENTION

Vapor cooled transformers, of the type described within U.S. patent application Ser. No. 843,676 are available as replacements for transformers containing polychlorinated biphenyls as one of the constituents of the dielectric coolant. The vapor cooled transformers utilize the dielectric properties of the coolant to insulate the core and windings of the transformer and the change of state properties of the coolant to transfer the heat from the core and windings to a heat exchanger. In order to compensate for the presence of any adsorbed noncondensable gases, such as air, the heat exchangers employed are substantially larger than the heat exchangers required with comparable rated oil filled units. The dissolved noncondensable gases within the coolant become separated from the coolant within the heat exchanger during the condensation cycle of the coolant. The separated noncondensable gases within the heat exchanger form air pockets within the heat exchanger cooling tubes adversely preventing the coolant from entering some of the tubes. The large size of the heat exchangers associated with vapor cooled transformers assures adequate available area for receiving the coolant for the projected life of the transformer.

The purpose of this invention is to provide vapor cooled transformers having heat exchangers of a reduced size by providing accurate means for determining the presence of air leaks within the transformer and for preventing the accumulation of air both within the transformer and the heat exchanger.

SUMMARY OF THE INVENTION

The invention comprises a pair of calibrated cylinders interconnected by means of a valve wherein one of the cylinders contains a pressure gauge and the other cylinder contains an inlet valve. The cylinders are used to determine the concentration of air within the condensable coolant used in vapor cooled transformers. A sample of condensable coolant is allowed to fill one of the cylinders and the cylinder is valved to the atmosphere. The interconnecting valve is then opened and the coolant is allowed to come to thermal equilibrium within both cylinders. Observations of the pressure within the cylinders by means of a pressure gauge as well as the ambient temperature, allows the quantity of dissolved air to be determined using Henry's Law.

DESCRIPTION OF THE PREFERRED EMBODIMENT

Figure 1:
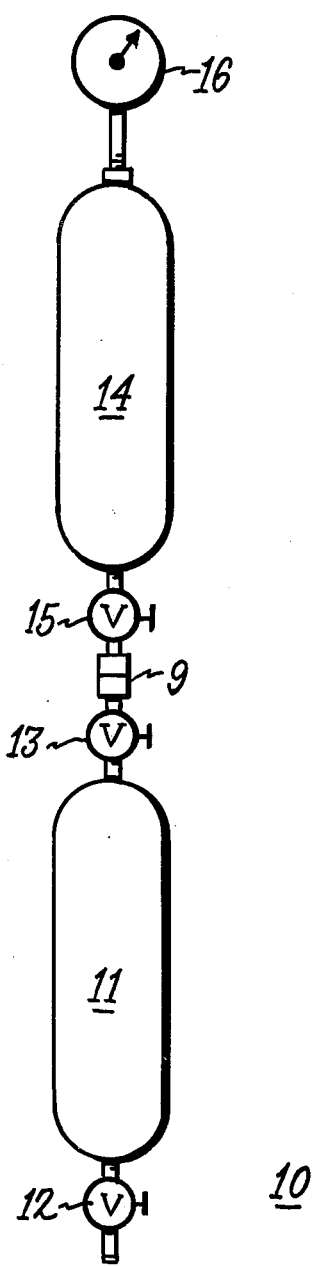
FIG. 1 is a diagrammatic representation of the gas sampling apparatuus of the instant invention.

FIG. 1 shows a sampling system 10 consisting of a first cylinder 11 having a first valve 12 and a second valve 13. First cylinder 11 is connected with a second cylinder 14 by means of a fitting 9 and an interconnecting valve 15. A gauge 16 is connected to one end of second cylinder 14 and is calibrated to read total pressure.

Sample system 10 is used for determining the quantity of noncondensable gas dissolved within the condensable coolant used in a vapor cooled transformer in the following manner. Both cylinders 11 and 14 are evacuated and valves 12, 13, and 15 are closed. Cylinder 11 is connected with a source of condensable coolant such as the trichlorotrifluoroethane used within vapor cooled transformers as described within the aforementioned U.S. patent application and cylinder 11 is completely filled with a sample of the coolant containing dissolved noncondensable gases by means of valve 12. After cylinder 11 is filled with the sample coolant, valve 12 is closed and valves 13 and 15 are open so that the coolant comes to thermal equilibrium between the pressure exerted by its liquid and vapor phases. The equilibrium pressure at gauge 16 represents the total pressure within cylinders 11 and 14. The total pressure $P_t$ consists of the vapor pressure of the coolant and partial pressure of the dissolved noncondensable gas contained within the coolant. The concentration of dissolved noncondensable gas X is given by the expression $X = H(T)[P_t - P(T)]$. $P(T)$ represents the vapor pressure of the condensable coolant at the given temperature. Henry's Constant $H(T)$ is readily available from vapor pressure curves supplied by the manufacturers of the condensable coolants employed.

The expression for X shows, therefore, that the concentration of dissolved noncondensable gas in the coolant is a direct function of the difference between the total pressure $P_t$ measured at gauge 16 and the vapor pressure $P(T)$ of the coolant at a given temperature T. When vapor cooled transformers develop a leak either in the transformer tank or the heat exchanger assembly, the gas entering the transformer generally comprises air. Sampling the transformer coolant over intervals of operating time will also indicate the rate at which the dissolved gas is increasing within the coolant and give an approximate indication of the size of the leak.

When the vapor cooled transformer comprises an assembly wherein the condensable coolant is contained within the windings in a closed system and dielectric gas such as sulphur hexafluoride, ($SF_6$) is used to insulate the transformer windings, the $SF_6$ gas can leak into the coolant. Measuring samples of the coolant over intervals of time would therefore provide an indication of whether an $SF_6$ leak exists and the rate at which $SF_6$ is leaking into the coolant.

TABLE I

| T (°F.) | $X_{(meas.)}$ | Pt (Psia) | P (T) | $P_{(air)}$ | X (calc.) |
|---|---|---|---|---|---|
| 71 | .0206 | 18.2 | 5.5 | .87 | .0195 |
| 72 | .0150 | 14.7 | 5.5 | .63 | .0148 |
| 75 | .0088 | 13.7 | 5.9 | .60 | .012 |
| 72 | .0055 | 13.7 | 5.5 | 1.26 | .011 |
| 75 | .0021 | 14.2 | 5.7 | 1.11 | .011 |

Table I shows some measured values of X obtained with air and with $SF_6$ dissolved within the coolant which comprises trichlorotrifluoroethane $Cl_3F^3C_2$. X is expressed as the number of moles of $SF_6$ per mole $Cl_3F_3C_2$ in liquid phase.

System 10 of FIG. 1 can also be used as an analytical tool to determine not only the magnitude of a leak within a vapor cooled transformer but can also be used to determine the nature of the dissolved gas.

Figure 2:
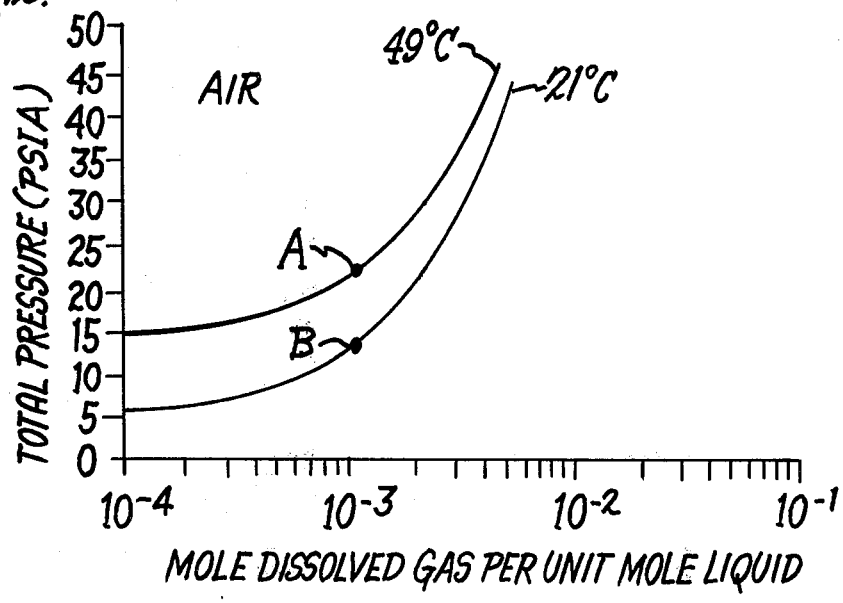
FIG. 2 is a graphic representation of the total system pressure as a function of air concentration at two equilibrium temperatures within the apparatus of FIG. 1.
Figure 3:
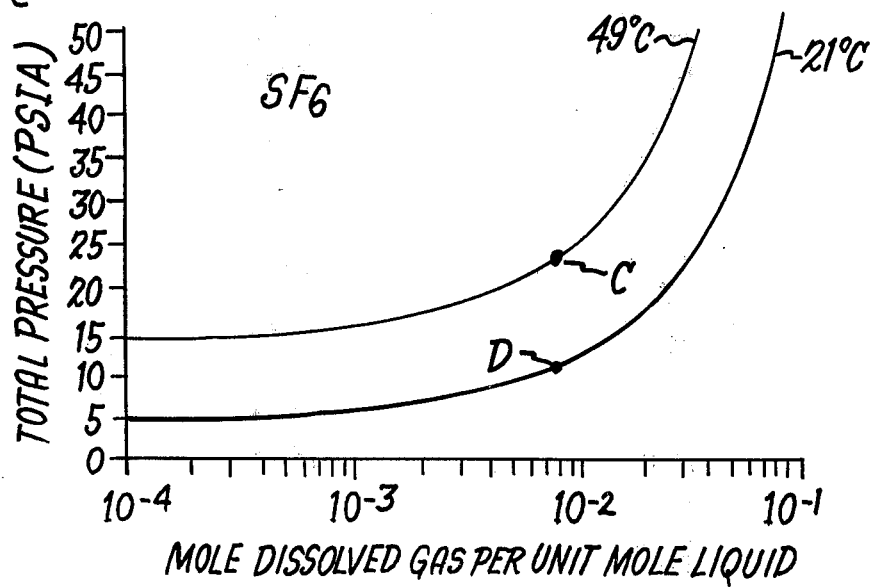
FIG. 3 is a graphic representation of total system pressure as a function of $SF_6$ concentration at two equilibrium temperatures within the apparatus of FIG. 1.

FIG. 2 and FIG. 3 for example, shows the total pressure exerted by two noncondensable gases in the coolant as a function of dissolved gas concentration. Since both the concentration of the gas dissolved in the coolant and the total pressure in the space above the coolant within cylinders 11 and 14 of FIG. 1 are both functions of the temperature, gas concentration measurements taken at two different temperatures can provide an indication of the identity of the dissolved gas.

With cylinders 11 and 14 within a constant temperature bath so that the coolant sample contained therein comes to thermal equilibrium at a particular temperature, the pressure at gauge 16 is recorded. With cylinders 11 and 14 removed from the constant temperature bath and allowed to come to thermal equilibrium at room temperature, the pressure at gauge 16 is again recorded to give two different values of total pressure.

Since the total mass of noncondensable gases within cylinders 11 and 14 is constant irrespective of system temperature, the total concentration of the noncondensable gas is also independent of system temperatures. FIGS. 2 and 3 denote the variation in total system pressure as a function of the concentration of two noncondensable gases, air and $SF_6$, at two different system temperatures, 21° C. and 49° C. Using the data depicted in FIGS. 2 and 3, the following procedure can be employed both to determine the total amount of noncondensable gas dissolved in the condensable coolant as well as to provide a qualitative approximation as to which gas is present. This is obtained by taking a first pressure reading at gauge 16 at one equilibrium temperature and a second pressure reading at gauge 16 at a second equilibrium temperature. As an example of a qualitative noncondensable gas determination, the following pressure readings were obtained from gauge 16 at two different temperatures. A pressure reading of 21.0 PSIA was obtained from gauge 16 at an equilibrium system temperature of 49° C. shown at point A in FIG. 2 corresponding to a concentration of $1 \times 10^{-3}$ moles dissolved noncondensable gas per unit condensable liquid. A pressure reading of 12.0 PSIA was obtained from gauge 16 at an equilibrium system temperature of 21° C. shown at B to correspond to the same concentration of $1 \times 10^{-3}$ moles. Since FIG. 2 is a calibrated partial pressure relationship for air, this is an indication that the dissolved noncondensable gas in the condensable liquid is air. From the data shown in FIG. 3 the concentration of $SF_6$ in the liquid at a system equilibrium temperature of 49° C. at a pressure of 21 PSIA, shown at C, would be $8 \times 10^{-3}$ moles. However, at an equilibrium system temperature of 21° C. the total pressure corresponding to a concentration of $8 \times 10^{-3}$ moles should be 10 PSIA shown at D. This indicates, therefore, that the dissolved noncondensable gas is air rather than $SF_6$. Since vapor cooled devices are generally employed in atmospheres which are likely to be subjected to $SF_6$ or air leaks, the possibility is high that the dissolved noncondensable gas would most likely be air or $SF_6$. Mixtures of both air and $SF_6$ dissolved within the same condensable liquid would appear at pressure values both above and below the curves indicated at FIGS. 2 and 3 for air and $SF_6$ but would be at the same concentration for both values. In the event of a mixture of both air and $SF_6$ dissolved within the condensable coolant the method of the invention could therefore indicate that such a mixture exists but would not, without extensive calibration, determine the relative concentrations of each component.

A simplified arrangement for sampling the coolant and determining the coolant and noncondensable gas pressure would consist of a single valved cylinder containing a calibrated pressure gauge. The pressures can be determined in a manner similar to that described for the two cylinder embodiment. The contribution of trapped air within the single cylinder would present a larger error than in the two cylinder large volume embodiment, however.

I claim:

1. A method for determining the concentration of dissolved gas in condensable power transformer coolants comprising the steps of:
   providing container means in fluid coupled relation with a power transformer tank;
   evacuating the container means;
   admitting a sample of condensable coolant from the transformer tank to completely fill the container means;
   closing the container means to allow the coolant and any noncondensable gas dissolved therein to achieve a state of thermal equilibrium within the container means;
   measuring the total pressure within the container means; and
   measuring the temperature of the sample in its state of thermal equilibrium;
   whereby the concentration of dissolved noncondensable gas in the sample is determined by Henry's Law.

2. The method defined in claim 1, which further includes the steps of subjecting the container means to a different temperature environment;
   again allowing the coolant and the noncondensable gas dissolved therein to achieve a new state of thermal equilibrium within the container means;
   again measuring the total pressure within the container means and the temperature of the sample in its new state of thermal equilibrium;
   whereby to provide an indication of the identity of the noncondensable gas.

3. The method defined in claims 1 or 2, wherein the container means consists of a pair of separate containers in selectively controlled fluid coupled relation, said sample being admitted to initially fill one container and then allowed to achieve thermal equilibrium in both containers.

4. The method defined in claim 1 or 2 wherein the coolant is a fluorinated hydrocarbon and the dissolved gas may be at least one of the group including sulfur hexafluoride, nitrogen and air.

5. The method defined in claim 3 wherein the coolant is a fluorinated hydrocarbon and the dissolved gas may be at least one of the group including sulfur hexafluoride, nitrogen and air.

* * * * *